United States Patent
Goodson, III et al.

(10) Patent No.: US 7,826,053 B2
(45) Date of Patent: Nov. 2, 2010

(54) MULTI-PHOTON ABSORPTION DETECTION OF MATERIALS

(75) Inventors: Theodore Goodson, III, Ann Arbor, MI (US); Oleg Varnavski, Ypsilanti, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/865,513

(22) Filed: Oct. 1, 2007

(65) Prior Publication Data
US 2008/0079937 A1  Apr. 3, 2008

Related U.S. Application Data

(60) Provisional application No. 60/848,416, filed on Sep. 29, 2006.

(51) Int. Cl.
  G01J 3/443 (2006.01)
  G01N 21/63 (2006.01)
  G01N 21/64 (2006.01)
(52) U.S. Cl. ..................... 356/318; 356/417
(58) Field of Classification Search .............. 356/317, 356/318, 417
  See application file for complete search history.

(56) References Cited

U.S. PATENT DOCUMENTS

| 6,537,829 B1 | 3/2003 | Zarling et al. |
| 2004/0259023 A1 | 12/2004 | Campagnola et al. |
| 2005/0157301 A1 | 7/2005 | Chediak et al. |
| 2006/0092414 A1 | 5/2006 | Geshwind et al. |
| 2006/0144126 A1 | 7/2006 | O'Brien et al. |

OTHER PUBLICATIONS

Wille et al., Teramobile: A mobile femtosecond-terawatt laser and detection system, The European Physical Journal Applied Physics, vol. 20, 2002, pp. 183-190.*
Mejean et al. Remote detection and identification of biological aerosols using a femtosecond terawatt lidar system, Applied Physics B Lasers and Optics, vol. 78, 2004, pp. 535-537.*
International Search Report for PCT/US07/80049 dated Mar. 28, 2008.
"Multiphoton Fluorescence Excitation: New Spectral Windows for Biological Nonlinear Microscopy"; by: Chris Xu; Warren Zipfel; Jason B. Shear; Rebecca M. Williams; Watt W, Webb; *Proceedings of the National Academy of Sciences of the United States of America;* vol. 93, No. 20 (Oct. 1, 1996), pp. 10763-10768.

* cited by examiner

*Primary Examiner*—F. L Evans
(74) *Attorney, Agent, or Firm*—Rader, Fishman & Grauer PLLC

(57) ABSTRACT

An exemplary embodiment includes an apparatus having an energy source for selectively directing a first energy toward a first material. The at least a portion of the first energy excites a preselected second material to an excited state where at least two photons of the first energy are absorbed by the molecule of the second material causing the molecule to emit a second energy at about a predetermined wavelength. The apparatus also includes a control system for directing the first energy toward the first material. The apparatus also includes a detector for detecting at least a portion of the emitted second energy when the detector is more than about 40 meters from the molecule.

26 Claims, 8 Drawing Sheets

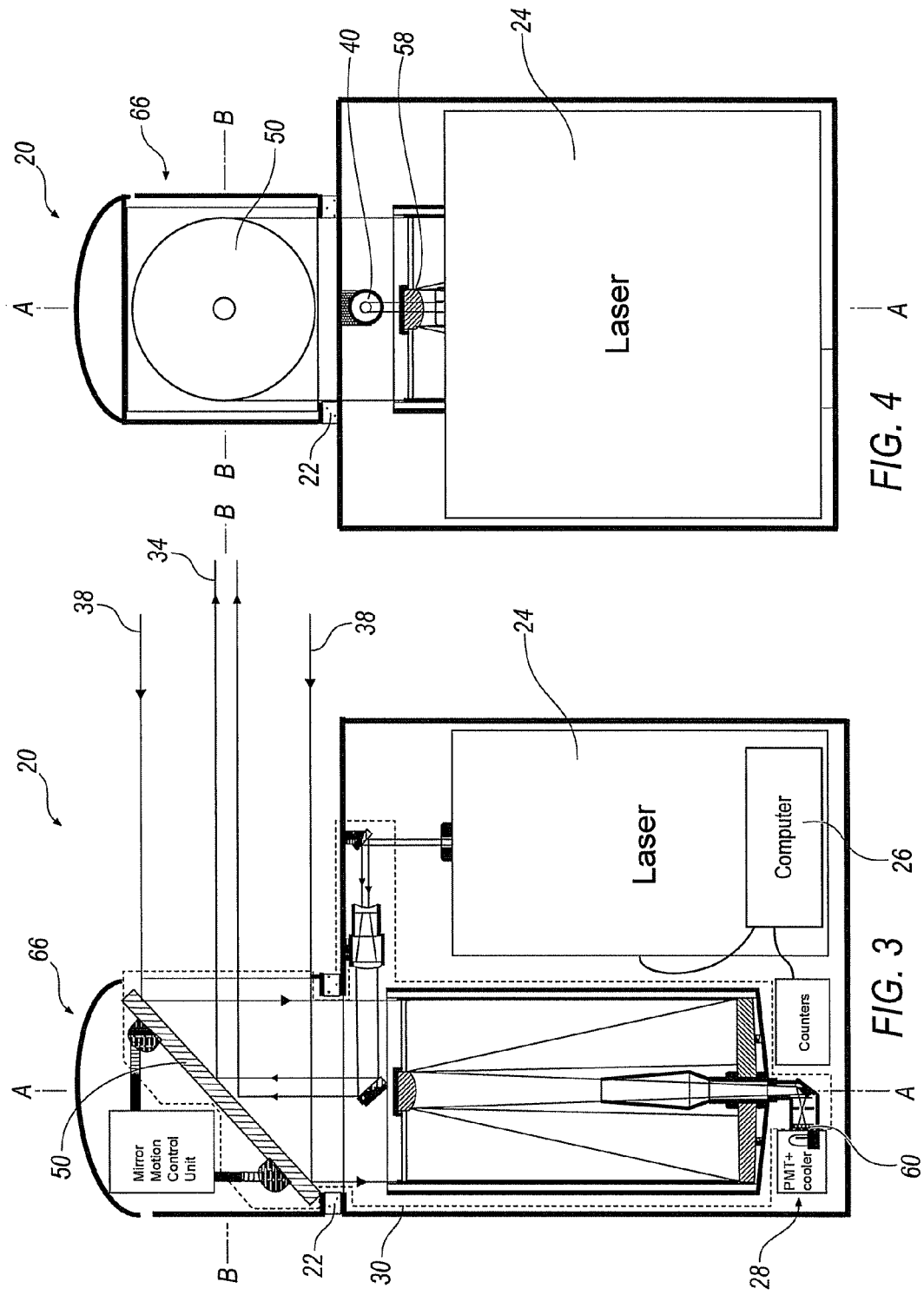

US 7,826,053 B2

MULTI-PHOTON ABSORPTION DETECTION OF MATERIALS

CROSS REFERENCE TO RELATED APPLICATIONS

This application claims priority to U.S. Provisional Patent Application 60/848,416, filed Sep. 29, 2006, the disclosure of which is incorporated by reference in its entirety.

TECHNICAL FIELD

The disclosure generally relates to remote optical detection of energetic materials.

BACKGROUND

Detection of materials using spectroscopy has been used for identifying materials. Applications such as identification of atmospheric pollutants from the ground and identification of particles on the surface of a planet typically rely on identifying high concentrations of particles, and are unreliable for identification of minute quantities of particles, or vaporized compounds. Identification of minute quantities is typically limited to short distances (generally less than a few feet).

Raman scattering is a phenomenon that may be used to identify some particles. Briefly, Raman scattering may induced by directing a laser at a material and permitting the material to absorb a photon as an atom or molecule is altered to an energized state. When the material subsequently emits the photon, the energy of emission will release light and a detector may be used to perform a spectral analysis of the light. However, since the energy emitted is proportional to the energy absorbed, Raman scattering requires a very intense laser and/or use of a laser source in the ultraviolet for detection beyond a few feet.

The use of ultraviolet light is disfavored in detection equipment used in unrestricted areas due to the potential for eye damage from receiving light with a wavelength below the visible spectrum. Therefore, identifying a material remotely using the Raman effect may be impractical when the laser source is broadly directed toward personnel. Generally, the use of light with wavelengths in the visible spectrum and above (infrared) does not present the concern of eye damage. Accordingly, there exists a need for a remote detection device that would not be harmful to the eye and is capable of detecting minute particles over relatively large distances.

BRIEF DESCRIPTION OF THE DRAWINGS

Referring now to the drawings, preferred illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are not intended to be exhaustive or otherwise limit or restrict the claims to the precise forms and configurations shown in the drawings and disclosed in the following detailed description.

FIG. 3 is a view of a portion of FIG. 1.

FIG. 4 is a side view of the detector of FIG. 1.

DETAILED DESCRIPTION

Figure 1:
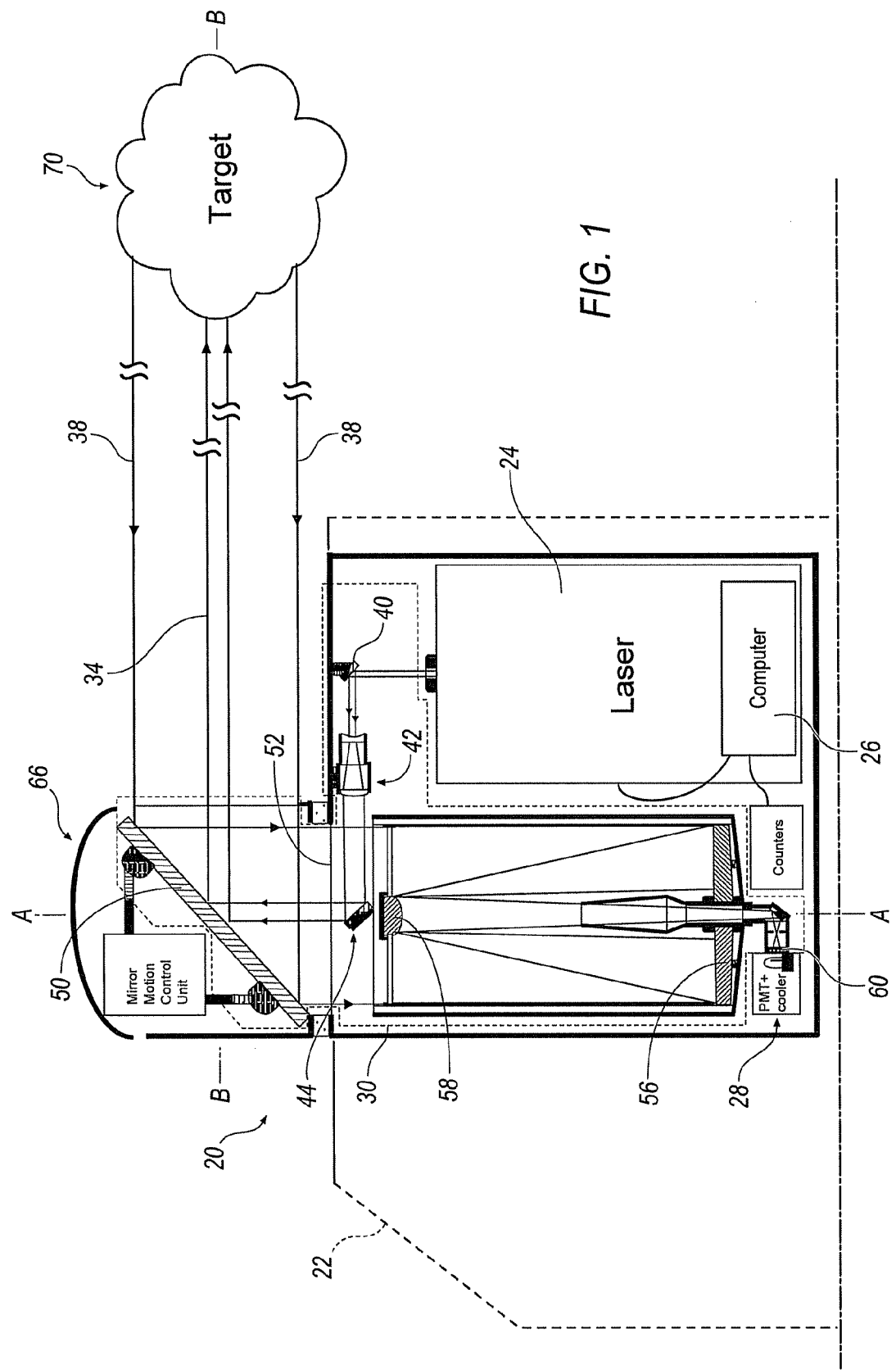
FIG. 1 is a schematic plan view of a detector.

FIG. 1 illustrates a detection system 20. In the embodiment illustrated, the detection system 20 may be portably mounted within a vehicle 22 and includes a laser 24, a control system 26, a detector 28, and a reflection and collection system (RCRS) 30. The laser 24 is positioned to send a beam of collimated light 34 toward the RCRS 30. The detector 28 receives energy 38 from the RCRS 30, as discussed in greater detail below.

As best seen in FIG. 3, the RCRS 30 includes a first laser reflector 40, a lens system 42, a second laser reflector 44, a main reflector 50, a main window 52, a first collector reflector 56, a second collector reflector 58, and a filter 60. In the embodiment illustrated, the main reflector 50 is rotatably mounted to a mirror control unit 66 that is, in one illustrative embodiment, rotatable about axis A-A relative to the vehicle 22 and the balance of the detection system 20. The mirror control unit may also be tilted with respect to the A-A axis during rotation to permit detection in a three dimensional array.

Figure 2:
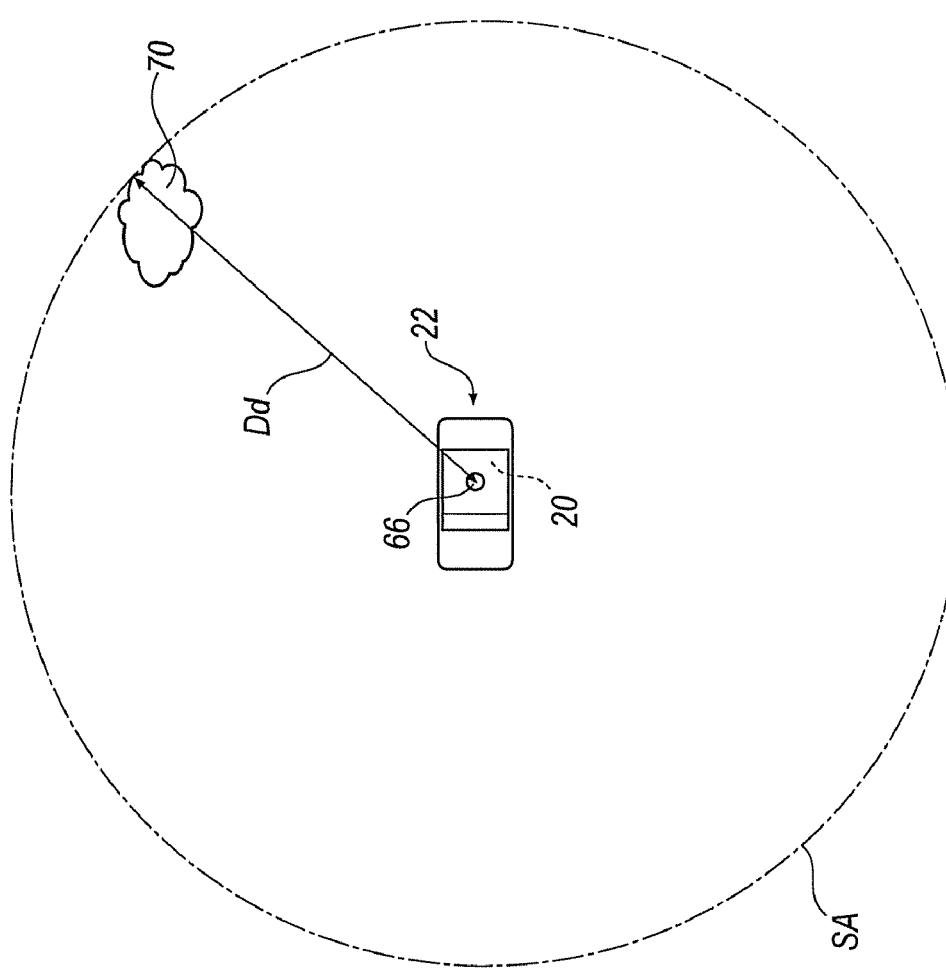
FIG. 2 is a top view of a scanning area of the detector of FIG. 1.
Figure 5:
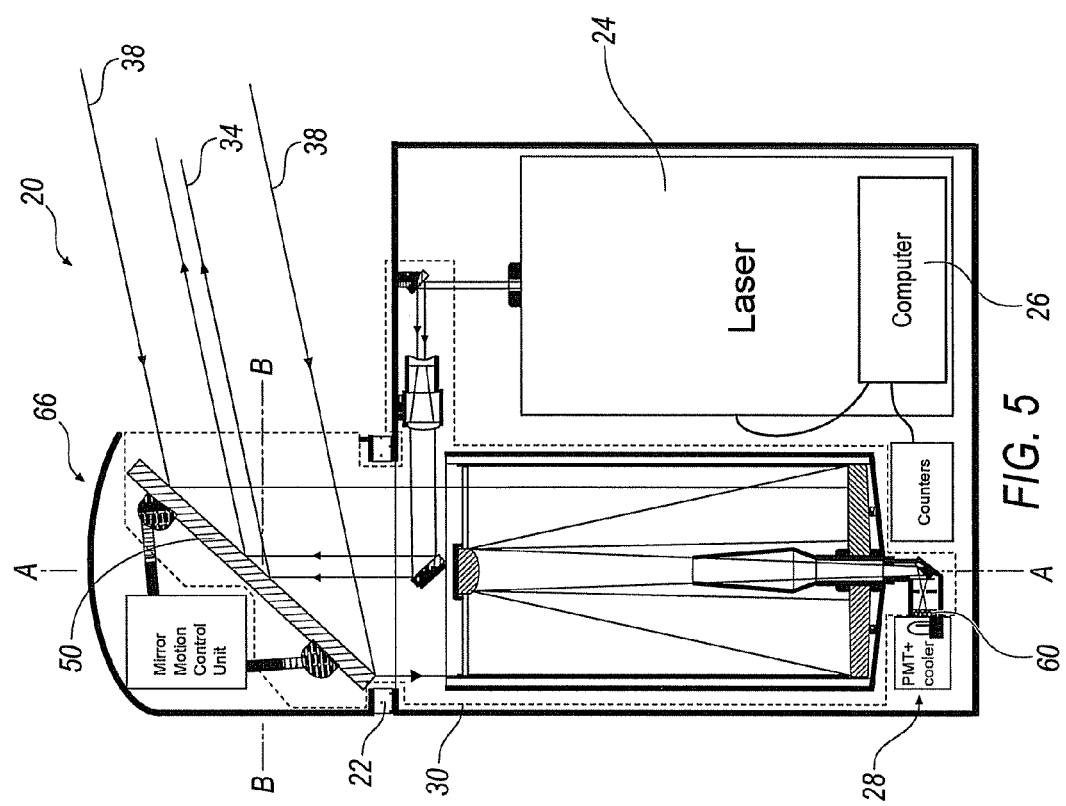
FIG. 5 is a side view of the detector of FIG. 1

To briefly describe the operation of the detection system 20, light is emitted from the laser 24 to direct the beam 34 toward the first laser reflector 40. The beam 34 is reflected by the first laser reflector 40 through the lens system 42 and onto the second laser reflector 44. The beam 34 is then reflected by the second laser reflector 44 through the main window 52, toward the main reflector 50. The main reflector 50 reflects the beam 34, as best seen in FIG. 1, toward a desired target 70 at a distance $D_d$, as best seen in FIG. 2. The beam 34 interacts with the target 70, as discussed in greater detail below, to emit energy.

For purposes of this discussion, the target 70 is the air surrounding an item of interest where the air includes materials that have a vapor pressure value that would result in quantities of the material to vaporize and dissolve into the atmosphere around the item, although the target 70 may also be surface particulate, solids, liquids, gasses, or any material form.

The energy emitted will generally be emitted in random directions from the target 70, with a portion of the energy (schematically illustrated as energy 38) reaching the main reflector 50. The energy 38 is reflected by the main reflector 50, through the window 52, toward the first collector reflector 56. At least a portion of the energy 38 is then reflected by the first collector reflector 56 toward the second collector reflector 58. Then, at least a portion of the energy 38 is then reflected by the second collector reflector 58 toward the detector 28. In the embodiment illustrated, the filter 60 is positioned within the detector 28 such that the energy 38 passes through the filter 60 prior to detection, as discussed in greater detail below.

As best seen in FIGS. 1-5, rotation of the mirror control unit 66 about the axis A-A will result in the beam 34 directed in a 360° path generally within plane B-B to define a scanned area SA (FIG. 2) that surrounds the vehicle 22. In the embodiment illustrated, the laser 24 is a pulsed laser with about a 100 femto-second (fs) pulse, although suitable pulses of lesser or greater magnitude may be used. Further, the laser 24 in the embodiment illustrated has a power of about 5 micro Joules (mJ) at about 500 kilohertz (KHz) at about 800 nanometers (nm), although other lasers of suitable output may also be used. For example, laser 24 may emit light of shorter wavelengths (higher energy) and may have a power of about less than 50 micro Joules, or less than about 30 micro Joules. Importantly, the laser 24 output is not of a level to harm the eye (800 nm is infrared). That is, the laser output is not necessarily in the ultraviolet range (below about 300 nm). For purposes of this discussion, visible light is taken to be in the spectrum of about 300 to about 700 nm.

Accordingly, the target 70 can be in any direction from the detection system 20 that the RCRS 30 can direct the beam 34 toward. While the mirror control unit 66 is illustrated as rotating about the axis A-A which will result in the beam 34 directed in a 360° path about the vehicle 22 to detect within the area SA, the mirror control unit 66 may be modified to scan in planes other than plane B, and may be modified to oscillate about axis A-A while the beam 34 is directed to targets above and/or below plane B.

Figure 6:
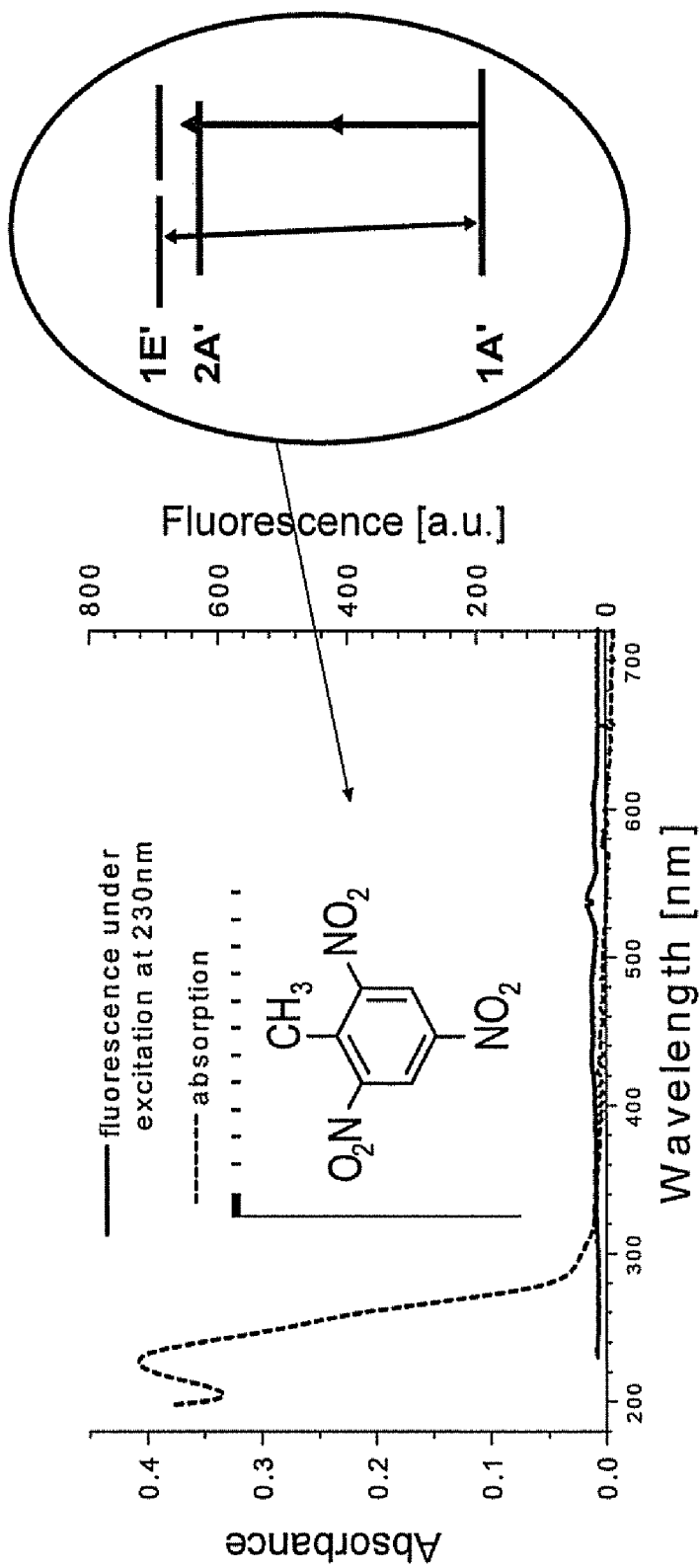
FIG. 6 is a graphical representation of the absorption and emission of a single photon prior art system.

FIG. 6 illustrates a prior art one-photon absorption excitation where trinitrotoluene (TNT) molecules absorb one photon of energy and emit one photon of energy for each absorption event. In the illustration of 6, a laser bombards a TNT molecule with photons of about 230 nm to excite the TNT molecule as the photon is absorbed. The resulting emission of a lower energy photon (longer wavelength) produces a minimal fluorescence that is within the visible spectrum, but less than about 40 arbitrary units (au).

Figure 7:
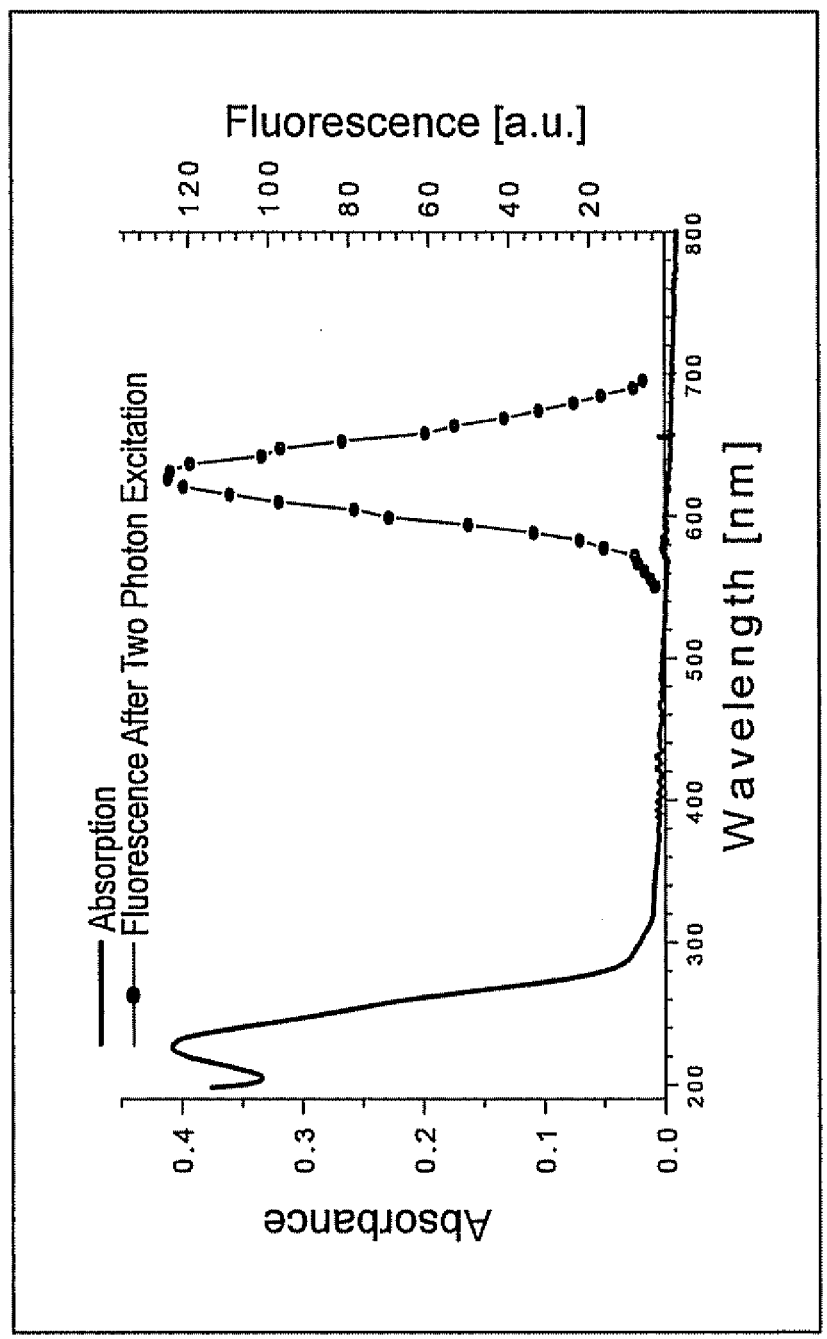
FIG. 7 is a graphical representation of the absorption and emission of a multi-photon system.

FIG. 7 illustrates a two-photon absorption (TPA), excitation where a greater amount of energy is emitted. In the illustration of FIG. 7, a laser bombards a TNT molecule with photons of about 230 nm to excite the TNT molecule as two photons are absorbed. Typically, the laser emits a frequency of about 400 nm or about 800 nm to drive this excitation. The absorbance of the TNT molecules is illustrated as identical as in the one-photon absorption, although the TNT molecule emits a TPA excited energy at around 630 nm with a fluorescence of about 120 au.

This TPA excited energy is emitted in all directions with at least a portion of the total energy (energy 38) being directed toward the main reflector 50. The energy 38 is directed to the detector 28 by the RCRS 30, as discussed above. In the embodiment illustrated, the detector 28 includes a photomultiplier tube, although other suitable systems may be used. In operation, the detector 28 is essentially a photon counter that registers photons within a range of energies of interest. Importantly, the laser 24 and detector 28 may be adjustable to enable the detection system 20 to detect different atoms or molecules of interest. The detector may be a commercially available photon counter, as known to those of skill in the art.

In the exemplary embodiment illustrated, the control system 26 includes a microprocessor (not shown) that controls the rotational speed of the mirror control unit 66, the output of the laser 24, and the detector 28. The control system 26 may, based upon the rotational position of the main reflector 50 and the vehicle 22, record the direction (from the vehicle 22) that the target 70 is in when the target 70 is initially detected. As the vehicle 22 travels, a second detection of the target 70, and the direction relative to the vehicle 22 may be recorded. The control system 26 may then identify the position of the target 70 by triangulation and notify an operator of the position of the detected target 70. Importantly, the control system 26 may also include a global positioning system (GPS) receiver to identify the location of the target 70.

The control system 26 may also record the strength of the energy received when the target 70 is detected, and, based upon a distance calculated by triangulation, estimate the concentration of the target 70 in the air. One illustrative example of a use for the detection system 20 is for detection of an improvised explosive device (IED), which typically would have a surrounding atmosphere that contains minute particles of explosives.

Two-photon absorption, as distinguished from the Raman effect, is experienced by an atom or molecule, such as the target 70, as two photons of light are absorbed and a higher order of energy is emitted. Generally, the wavelength of the energy depends upon the material. TPA detection is typically used when a laser is directed toward a material that will absorb two photons of light before emitting energy. When two photons are absorbed, the energy emission is proportional to the square of the power of the laser. An illustrative example of TPA phenomena is found in "*Multiphoton Fluorescence Excitation: New Spectral Windows for Biological Nonlinear Microscopy*," Proceedings of the National Academy of Sciences of the United States of America, Vol. 93, No. 20. (Oct. 1, 1996), pp. 10763-10768; and "*Two-photon absorption of $F_2^-$ color centers in LiF crystal at 1906 nm*," Laser Physics Letters, 1, No. 4, (2004), pp. 163-166.

Generally, the amount of energy emitted in TPA increases with an increase in the TPA cross section of a target, such as the target 70. That is, a material with a high TPA cross section will emit a greater amount of energy when exposed to a photon source, such as the laser 24. It has been found that TNT exhibits a favorable TPA cross section, That is, TNT molecules can be excited by a laser to absorb two or more photons before emission of energy. Since the energy emission is proportional to the square of the power of the laser 24, a lower power laser is required to produce a detectable energy emission when compared to a one-photon absorption emission of energy. This lower power laser permits the excitation of molecules over distance $D_d$ with a laser that may not be harmful to the human eye. Additionally, with a greater amount of energy emitted in TPA, the energy can be detected at greater distances, such as the distance $D_d$, when compared to a one-photon absorption emission of energy.

Detection of minute quantities of materials is possible if a material is sufficiently exposed to the atmosphere and the material has a vapor pressure that will permit a portion of the material to be present in the atmosphere surrounding the material. For example, it has been found that the vapor pressure of TNT in the atmosphere is determined to be about 1 part per billion (ppb). Therefore, TNT exposed to the atmosphere may be remotely detected with a detector that can identify TNT at a quantity of about 1 ppb. Many available techniques, such as Raman scattering are capable of detecting materials at no more than a few feet when using a laser source that is of lower energy than the ultraviolet.

In the illustrative example of a laser 24 (about 5 mJ at about 500 KHz at about 800 nm pulsed at about 100 fs) may TPA excite a target 70 (having about 1 ppb TNT) at a distance $D_d$ of about 400 meters (m) (1312 feet (ft)) from the main reflector 50 to the target 70 and may result in sufficient energy 38 reaching the detector 28 in order for the detector 28 to adequately identify the target 70 as containing TNT. Additionally, higher concentrations of TNT in the atmosphere may increase the capability of the detection system 20 such that the distance $D_d$ may increase. The vapor pressure of TNT may result in the local atmosphere having about 10 parts per billion (ppb) of TNT molecules, however, the saturation of particles in air or other media may vary.

Detector dark counts, or 'false counts' are due, at least in part, to random electronic noise that are detected by the detector as photons. In the embodiment illustrated, the filter 60 prevents at least some undesired energies, such as dark counts, from reaching the detector 28. Additionally, the filter 60 may filter any reflected beam 34 from the laser 24. Although the filter 60 is illustrated as a single filter, the filter 60 may be a multi-component system to condition the energy 38 where individual components (such as dispersive prisms, polarizers, etc.) eliminate portions of the undesired energy within energy 38. In the embodiment illustrated, the main window 52 has an anti-reflective coating on both sides to increase the quantum efficiency of the detector system 20, while protecting the portions of the detection system 20 that are inside the vehicle 22.

In the embodiment illustrated, particles of TNT in the atmosphere around a device containing TNT resulting from the vapor pressure of TNT are detected, although other materials may be detected by the detection system 20. That is, the detection system may be adjustable to detect more than one material, such as by selecting a material that will absorb more than one photon when excited with a selected laser emitting energy at a selected wavelength, and selecting a filter that will permit the passage of the emissions from the selected material.

Figure 8:
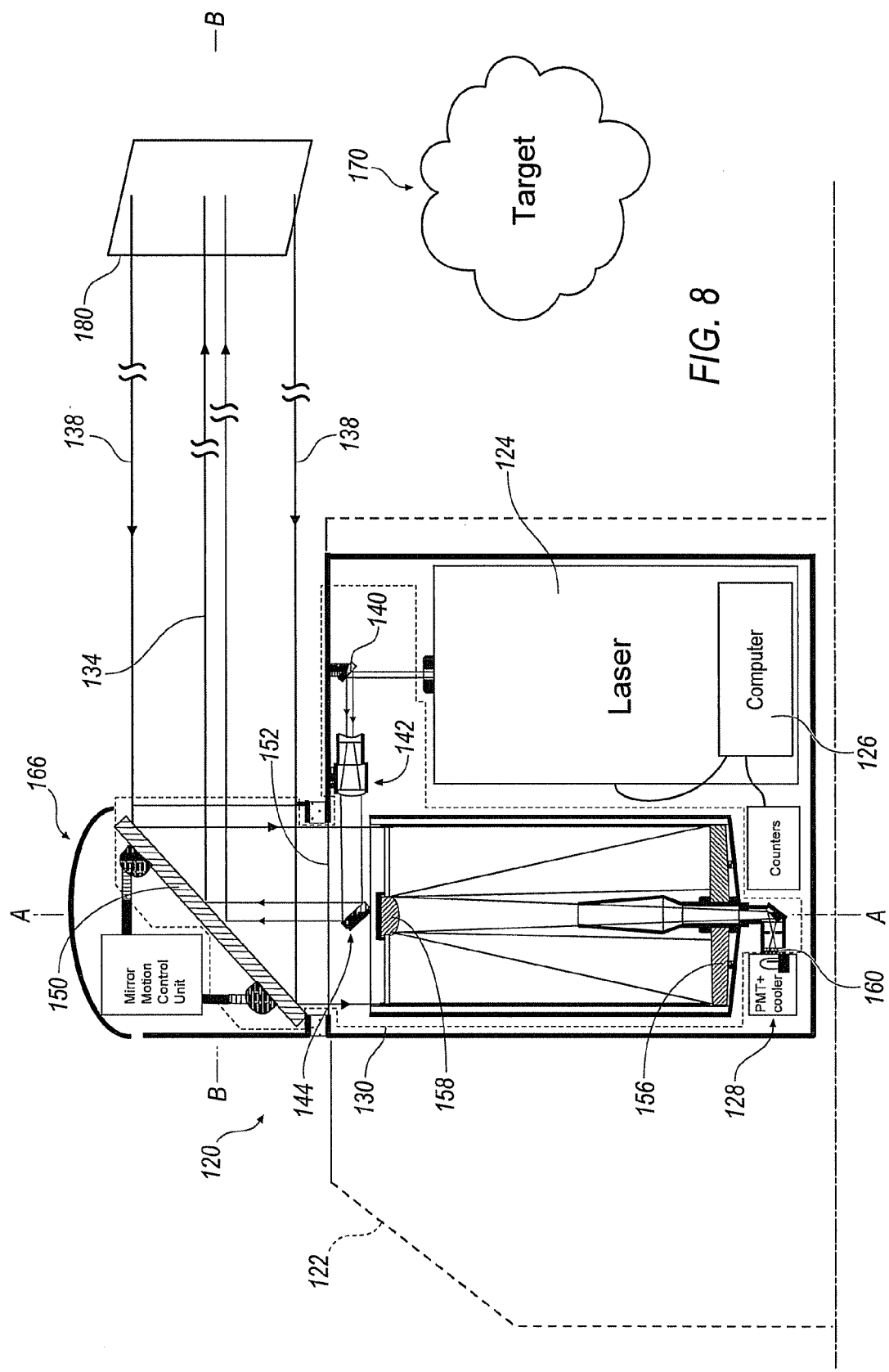
FIG. 8 is schematic side view of a detector.

In another embodiment a detection system 120 is schematically illustrated in FIG. 8. The detection system 120 may be portably mounted within a vehicle 122 and includes a laser 124, a control system 126, a detector 128, and a reflection and collection system (RCRS) 130. The laser 124 is positioned to send a beam of collimated light 134 toward the RCRS 130. The detector 128 receives energy 138 from the RCRS 130, as discussed in greater detail below.

As best seen in FIG. 8, the RCRS 130 includes a first laser reflector 140, a lens system 142, a second laser reflector 144, a main reflector 150, a main window 152, a first collector reflector 156, a second collector reflector 158, and a filter 160. In the embodiment illustrated, the main reflector 150 is rotatably mounted to a mirror control unit 166 that is, in one illustrative embodiment, rotatable about axis A-A relative to the vehicle 122 and the balance of the detection system 120. The mirror control unit 166 may also be tilted with respect to the A-A axis during rotation to permit detection in a three dimensional array.

To briefly describe the operation of the detection system 120, light is emitted from the laser 124 to direct the beam 134 toward the first laser reflector 140. The beam 134 is reflected by the first laser reflector 140 through the lens system 142 and onto the second laser reflector 144. The beam 134 is then reflected by the second laser reflector 144 through the main window 152, toward the main reflector 150. To detect a target 170, the main reflector 150 reflects the beam 134 toward a sensor 180 at a distance $D_d$. The beam 134 interacts with the sensor 180, which has been changed by interaction with the target 170, as discussed in greater detail below, to emit energy.

The energy emitted will generally be emitted in random directions from the sensor 180, with a portion of the energy (schematically illustrated as energy 138) reaching the main reflector 150. The energy 138 is reflected by the main reflector 150, through the window 152, toward the first collector reflector 156. At least a portion of the energy 138 is then reflected by the first collector reflector 156 toward the second collector reflector 158. Then, at least a portion of the energy 138 is then reflected by the second collector reflector 158 toward the detector 128. In the embodiment illustrated, the filter 160 is positioned within the detector 128 such that the energy 138 passes through the filter 160 prior to detection, as discussed in greater detail below.

Rotation of the mirror control unit 166 about the axis A-A will result in the beam 134 directed in a 360° path generally within plane B-B to define a scanned area SA (similar to FIG. 2) that surrounds the vehicle 122. In the embodiment illustrated, the laser 124 is a pulsed laser with about a 100 femtosecond (fs) pulse, although suitable pulses of lesser or greater magnitude may be used. Further, the laser 124 in the embodiment illustrated has a power of about 5 micro Joules (mJ) at about 500 kilohertz (KHz) at about 800 nanometers (nm), although other lasers of suitable output may also be used. For example, laser 124 may emit light of shorter wavelengths (higher energy) and may have a power of about less than 50 micro Joules, or less than about 30 micro Joules. Importantly, the laser 124 output is not of a level to harm the eye (800 nm is infrared). That is, the laser output is not necessarily in the ultraviolet range (below about 300 nm). For purposes of this discussion, visible light is taken to be in the spectrum of about 300 to about 700 nm.

Accordingly, the sensor 180 can be in any direction from the detection system 120 that the RCRS 130 can direct the beam 134 toward. While the mirror control unit 166 is illustrated as rotating about the axis A-A which will result in the beam 134 directed in a 360° path about the vehicle 122 to detect within the area SA, the mirror control unit 166 may be modified to scan in planes other than plane B, and may be modified to oscillate about axis A-A while the beam 134 is directed to targets above and/or below plane B.

This TPA excited energy is emitted in all directions with at least a portion of the total energy (energy 138) being directed toward the main reflector 150. The energy 138 is directed to the detector 128 by the RCRS 130, as discussed above. In the embodiment illustrated, the detector 128 includes a photomultiplier tube, although other suitable systems may be used. In operation, the detector 128 is essentially a photon counter that registers photons within a range of energies of interest. Importantly, the laser 124 and detector 128 may be adjustable to enable the detection system 120 to detect different atoms or molecules of interest. The detector may be a commercially available photon counter, as known to those of skill in the art. The 'counts', or number of photons detected, and/or the wavelength of the photons detected may be used to determine whether the system 120 has detected the target 170.

In the exemplary embodiment illustrated, the control system 126 includes a microprocessor (not shown) that controls the rotational speed of the mirror control unit 166, the output of the laser 124, and the detector 128. The control system 126 may, based upon the rotational position of the main reflector 150 and the vehicle 122, record the direction (from the vehicle 122) that the sensor 180 is in when the target 170 is initially detected. As the vehicle 122 travels, a second detection of the target 170, and the direction relative to the vehicle 122 may be recorded. The control system 126 may then identify the position of the target 170 by triangulation and notify an operator of the position of the detected target 170. Importantly, the control system 126 may also include a global positioning system receiver to identify the general location of the target 170.

Briefly, at least a portion of the material of the sensor 180, when exposed to the target 170 (a preselected material such as, for example, TNT) will experience a change that can be detected by the system 120. That is, the sensor 180, when not in the presence of the target 170, may exhibit a predictable response that may be detected by the detector 120. Further, the sensor 180, when in the presence of the target 170 (or recently in the presence of the target 170), may exhibit a predictable response that may be detected by the detector 120. The detections by the system 120 include counts and the wavelengths detected. A detection by the system 120 that is not consistent with the range of expected emissions for a sensor that has not been exposed tot the target 170 may indicate that the sensor 180 has been exposed to the target 170. The amount of deviation from the expected range may provide and indication of the concentration of the target 170 and or the amount of time that has elapsed since exposure to the target 170.

In an embodiment, the sensor 180 is selected such that at least a portion of the molecules of the sensor 180 have strong emission. Their emission will be quenched in the presence of TNT vapor. That is, molecules of the sensor 180 will normally have absorption and emission properties, but once these molecules interact with TNT, the excited molecules will return to the ground state (non-excited state) without emitting light. The sensor molecules in the presence of TNT will return to the ground state by a non-radiative pathway which might include vibrational relaxation or as heat.

In another exemplary embodiment, at least a portion of the material of the sensor 180 is a dendrimer that has a high response to TNT (Stem-Volmer quenching constant). The dendrimer will excite when exposed to TNT vapor and may emit visible light. Therefore, the sensor 180 may be visually observed to confirm the presence of TNT, Further, the TNT (or target 170) particles that interact with the dendrimer molecules may alter the molecules such that the system 120, when used to excite at least a portion of the sensor 180, may detect a change in the expected emission from the sensor 180. This detected change may be identified by the system 120, such as through the computer 126, and reported to a user. The change in expected emission may indicate the presence of TNT (even in vapor pressure in air concentrations) or may indicate tampering. The change in expected emission may indicate tampering with a sensor 180 or indicate that sensor 180 has been replaced or otherwise damaged.

In the event that the sensor 180 is exposed to the target 170, the system 120 need not detect the exposure immediately, since the change to the sensor 180 may not be completely reversible within a short amount of time. That is, the sensor 180 may be changed by the interaction with the target 170 immediately upon exposure and retain at least a portion of the change after the exposure has subsided (such as after a vehicle has passed the sensor 180).

The material of the sensor 180 may include Dendrimers or polymers that have strong fluorescence in the visible and near-IR spectral regions, although other suitable materials may be used. In one embodiment, the fluorescence of at least a portion of the material of the sensor 180 will be quenched in the presence of TNT. When the system excites a sensor 180 having unquenched material, the emissions from the sensor may be within an expected range of the amount of counts of emissions of the photons of the expected wavelength. When the system 120 excites the quenched material, the emissions detected by the system 120 may be lower than the expected range which may be indicative of exposure to TNT (since exposure to TNT may prevent at least a portion of the material from emitting photons of the expected wavelength).

Figure 10:
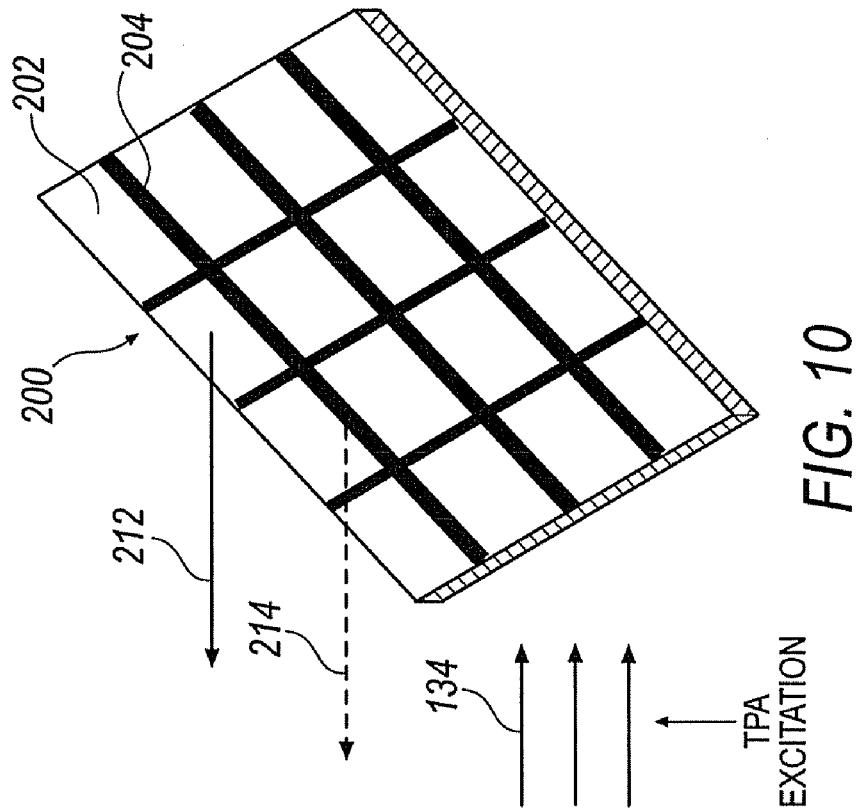
FIG. 10 is an enlarged perspective view of a portion of a sensor.
Figure 9:
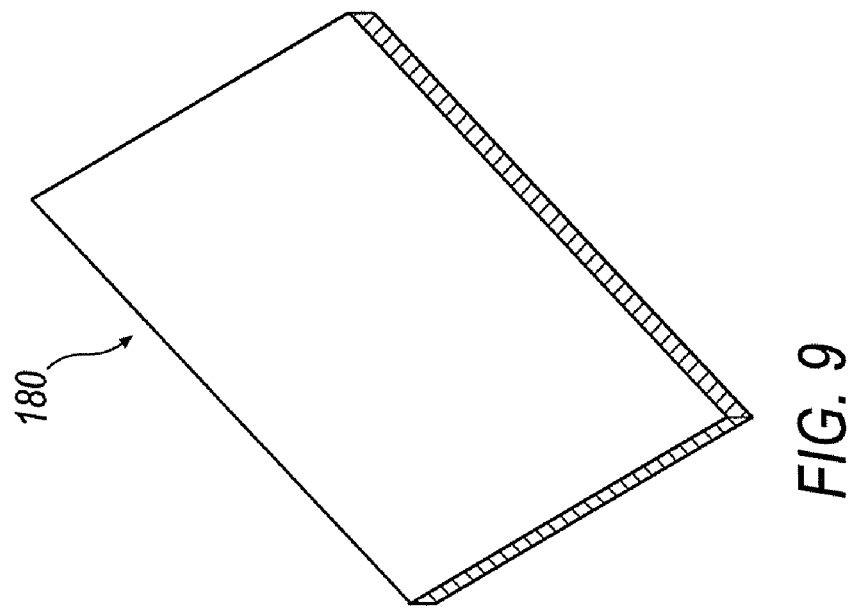
FIG. 9 is an enlarged perspective view of a portion of a sensor.

In another exemplary embodiment of the sensor 180, a sensor 200 is illustrated in FIG. 10. The sensor 200 includes a first material 202 and a second material 204. In the exemplary embodiment illustrated, the first material 202 will fluoresce when exposed to the target 170. The second material 204 is a material that may not significantly fluoresce (or may fluoresce differently than the first material 202) when exposed to the target 170. The second material 204 may be a dye applied to the first material 202, or other material that results in the first material 202 and the second material 204 being two different fluorescent species.

When the system 120 excites a sensor 200 that has not been exposed to a target 170 (directs beam 134 toward the sensor 200), the first material 202 will emit a first fluorescence 212 and the second material 204 will emit a second fluorescence 214. The filter 160 may filter out undesired wavelengths while splitting the wavelengths the first fluorescence 212 and the second fluorescence 214 into two differing streams. The different streams may be detected by two different detectors, such as detectors 128 adjusted to detect the wavelength of the stream, or may be detected by a single detector that can count streams of differing wavelength.

When the system 120 excites a sensor 200 that has been exposed to a target 170 (directs beam 134 toward the sensor 200), the first material 202 will emit a first fluorescence 212 and the second material 204 will emit a second fluorescence 214. However, since the fluorescence of the first material has been quenched, the amount of emissions of the first fluorescence 212 will be much lower when compared to the amount of emission of the second fluorescence 214. In this manner, the system 120 may detect the exposure of the sensor 200 to the target 170.

The difference in the wavelength and the amount of counts at each wavelength may indicate the amount of quenching by the target 170, which may indicate the concentration of the target 170 in air.

The detection of emissions from the second material 204 may be conducted simultaneously with detecting the emission from the first material 202. The first material 202 may be more sensitive to the target 170 than the sensitivity of the second material 204 to the target.

When exciting at least one molecule of the second material 204 with an energy, such as the beam 134, a third energy may be used that is at about the same wavelength as the beam 134, or may be a differing energy.

Although the reflection and collection systems discussed herein are described as including a single main reflector, the systems may include multiple reflectors, or no reflector, to obtain desired results. Further, the systems may rotate the reflectors at several thousand rpm, or may oscillate or sweep to scan a desired area.

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope. The scope of the invention is limited solely by the following claims.

What is claimed is:

1. An apparatus comprising:
    an energy source for selectively directing a first energy toward a first material, wherein at least a portion of the first energy excites a preselected second material to an excited state where at least two photons of the first energy are absorbed by the molecule of the second material causing the molecule to emit a second energy at a predetermined wavelength;

a multi-directional control system for directing the first energy toward the first material, wherein the control system includes a control unit for rotating at least a portion of the control system about an axis; and a detector for detecting at least a portion of the emitted second energy when the detector is more than about 40 meters from the molecule.

2. The apparatus of claim 1, wherein the control system includes:

a first reflector portion for reflecting the first energy from the energy source toward the first material; and a second reflector portion for reflecting the second energy from the first material toward the detector.

3. The apparatus of claim 1, wherein the control unit will tilt at least a portion of the control system with respect to the axis.

4. The apparatus of claim 1, wherein the energy source includes a laser with a power of below about 50 micro Joules.

5. The apparatus of claim 1, wherein the first material is a sensor portion that will excite when exposed to a preselected target material.

6. The apparatus of claim 1, wherein the detector will identify a change in the first material after exposure to a preselected target material when compared to the first material that has not been significantly exposed to the target material.

7. The apparatus of claim 1, wherein the energy source is a laser that selectively emits energy at a power of less than about 10 micro Joules in pulses of less than about 500 femtoseconds.

8. The apparatus of claim 1, further comprising a filter, wherein the filter permits passage of at least a portion of the second energy at a predetermined wavelength.

9. An apparatus comprising:

an energy source for selectively directing a first energy toward a first material, wherein at least a portion of the first energy excites a preselected second material to an excited state where at least two photons of the first energy are absorbed by the molecule of the second material causing the molecule to emit a second energy at about a predetermined wavelength;

a control system for directing the first energy toward the first material; and a detector for detecting at least a portion of the emitted second energy wherein the control system includes a first reflector portion for reflecting the first energy from the energy source toward the first material, and a second reflector portion for reflecting the second energy from the first material toward the detector, and wherein the control system further includes a control unit for rotating at least a portion of the control system about an axis.

10. The apparatus of claim 9, wherein the detector for detecting at least a portion of the emitted second energy detects when the detector is more than about 40 meters from the molecule.

11. The apparatus of claim 9, wherein the detector for detecting at least a portion of the emitted second energy detects when the detector is more than about 400 meters from the molecule.

12. The apparatus of claim 9, wherein the energy source is a laser that selectively emits energy at a power of less than about 10 micro Joules in pulses of less than about 500 femtoseconds.

13. The apparatus of claim 9, wherein the control unit will tilt at least a portion of the control system about the axis.

14. A method of detecting a preselected material comprising:

directing axially a first energy toward a target;

exciting at least one molecule of the target to an excited state where at least two photons are absorbed by the molecule, wherein the vapor pressure of the molecule is at about the vapor pressure of a selected second material; and detecting an emission from the molecule when the detector is more than about 40 meters from the molecule.

15. The method of claim 14, wherein directing includes directing the first energy toward the target when the molecule is less than a concentration of about 10 parts per billion (ppb).

16. The method of claim 14, wherein detecting includes detecting an emission from the molecule resulting from the two photon absorption at about a predetermined wavelength.

17. The method of claim 14, further comprising rotating at least a portion of a reflection system to deflect the first energy.

18. The method of claim 14, wherein directing includes directing the first energy in a wavelength above a spectrum of about 230 nano-meters (nm).

19. The method of claim 14, further comprising filtering to permit passage of an energy at about a predetermined wavelength, wherein detecting includes detecting at least the predetermined wavelength.

20. The method of claim 14, wherein exciting includes exciting a molecule that has been previously excited by a first material.

21. The method of claim 14, further comprising detecting an emission from a control material simultaneously with detecting the emission from the molecule, wherein the target is more sensitive to an energetic material than the sensitivity of the control material to the energetic material.

22. The method of claim 21, further comprising exciting at least one molecule of the control material with a third energy, wherein the third energy is at about the same wavelength as the first energy, and wherein the at least one molecule of the control material will emit a fourth energy.

23. An apparatus comprising:

an energy source for selectively directing a two photon energy toward a trinitrotoluene target material, wherein at least a portion of the two photon energy is absorbed by the molecules of the trinitrotoluene target material causing the molecule to emit a fluorescence energy at about a predetermined wavelength;

a control system for directing the two photon energy toward the trinitrotoluene target material; and a detector for detecting at least a portion of the emitted fluorescence energy wherein the control system includes a first reflector portion for reflecting the two photon energy from a energy source toward the trinitrotoluene target material, and a second reflector portion for reflecting the fluorescence energy from the trinitrotoluene target material toward the detector, and wherein the control system further includes a control unit for rotating at least a portion of the control system about an axis.

24. The apparatus of claim 23, wherein the two photon energy source is a laser emitting a frequency between about 400 nm to about 800 nm.

25. The apparatus of claim 23, wherein the trinitrotoluene target material fluorescence is a nitroaromatic producing compound.

26. The apparatus of claim 23, wherein the emitted fluorescence energy is about 630 nm.

* * * * *